United States Patent
Vaughan et al.

(10) Patent No.: US 12,053,187 B2
(45) Date of Patent: Aug. 6, 2024

(54) RECESSED BUR FOR A SURGICAL CUTTING TOOL

(71) Applicant: Stryker European Operations Limited, Carrigtwohill (IE)

(72) Inventors: Aidan Vaughan, Cork City (IE); Conor O'Shea, Innishannon (IE); Eoin Connolly, Dublin (IE); Fintan Tynan, Kilkenny (IE)

(73) Assignee: Stryker European Operations Limited, Carrigtwohill (IE)

( * ) Notice: Subject to any disclaimer, the term of this patent is extended or adjusted under 35 U.S.C. 154(b) by 538 days.

(21) Appl. No.: 17/415,108

(22) PCT Filed: Dec. 19, 2019

(86) PCT No.: PCT/IB2019/061139
§ 371 (c)(1),
(2) Date: Jun. 17, 2021

(87) PCT Pub. No.: WO2020/128980
PCT Pub. Date: Jun. 25, 2020

(65) Prior Publication Data
US 2022/0047276 A1 Feb. 17, 2022

Related U.S. Application Data

(60) Provisional application No. 62/781,836, filed on Dec. 19, 2018.

(51) Int. Cl.
*A61B 17/16* (2006.01)
(52) U.S. Cl.
CPC ...... *A61B 17/1615* (2013.01); *A61B 17/1628* (2013.01)

(58) Field of Classification Search
CPC .. A61B 17/32002; A61B 2017/320032; A61B 17/1624; A61B 17/1622;
(Continued)

(56) References Cited

U.S. PATENT DOCUMENTS 6,068,642 A    5/2000  Johnson et al.
7,011,661 B2   3/2006  Riedel et al.
(Continued)

FOREIGN PATENT DOCUMENTS

DE    9313604 U1    1/1994

OTHER PUBLICATIONS

International Search Report for Application No. PCT/IB2019/061139 dated Feb. 20, 2020, 3 pages.
(Continued)

*Primary Examiner* — Mohamed G Gabr
*Assistant Examiner* — Aman Kumar Mann
(74) *Attorney, Agent, or Firm* — Howard & Howard Attorneys PLLC

(57) ABSTRACT

A surgical cutting tool for use with a handpiece having a motor is disclosed. The surgical cutting tool comprises a nose tube defining a lumen between proximal and distal ends. A bushing is coupled to the nose tube at the distal end and is disposed at least partially within the lumen. The bushing defines a second lumen configured to receive a region of a driveshaft that extends past the distal end of the nose tube. A bur defines a recess sized to receive at least a portion of the bushing within the recess. The bur is configured to be coupled to the driveshaft within the recess.

15 Claims, 3 Drawing Sheets

(58) Field of Classification Search
CPC ........ A61B 17/1615; A61B 17/320016; A61B 2017/320004; A61B 17/1633
See application file for complete search history.

(56) References Cited

U.S. PATENT DOCUMENTS

| | | |
|---|---|---|
| 7,488,322 B2 | 2/2009 | Brunnett et al. |
| 7,879,037 B2 | 2/2011 | Brunnett et al. |
| 7,992,878 B2 | 8/2011 | Dace |
| 8,172,846 B2 | 5/2012 | Brunnett et al. |
| 9,186,157 B2 | 11/2015 | Brunnett et al. |
| 9,974,558 B2 | 5/2018 | O'Brien, II |
| 2005/0177168 A1 | 8/2005 | Brunnett et al. |
| 2006/0241630 A1 | 10/2006 | Brunnett et al. |
| 2009/0131940 A1* | 5/2009 | Brunnett ............ A61B 17/1624 606/80 |
| 2010/0286694 A1* | 11/2010 | Rio .................... A61B 17/1679 606/80 |
| 2011/0270293 A1* | 11/2011 | Malla ............... A61B 17/32002 606/180 |
| 2013/0072936 A1* | 3/2013 | To ...................... A61B 17/1671 606/79 |
| 2019/0262006 A1* | 8/2019 | Schwamb ........ A61B 17/32002 |

OTHER PUBLICATIONS

Machine-assisted English translation for DE 9 313 604 U1 extracted from the espacenet.com database on Aug. 20, 2021, 4 pages.

* cited by examiner

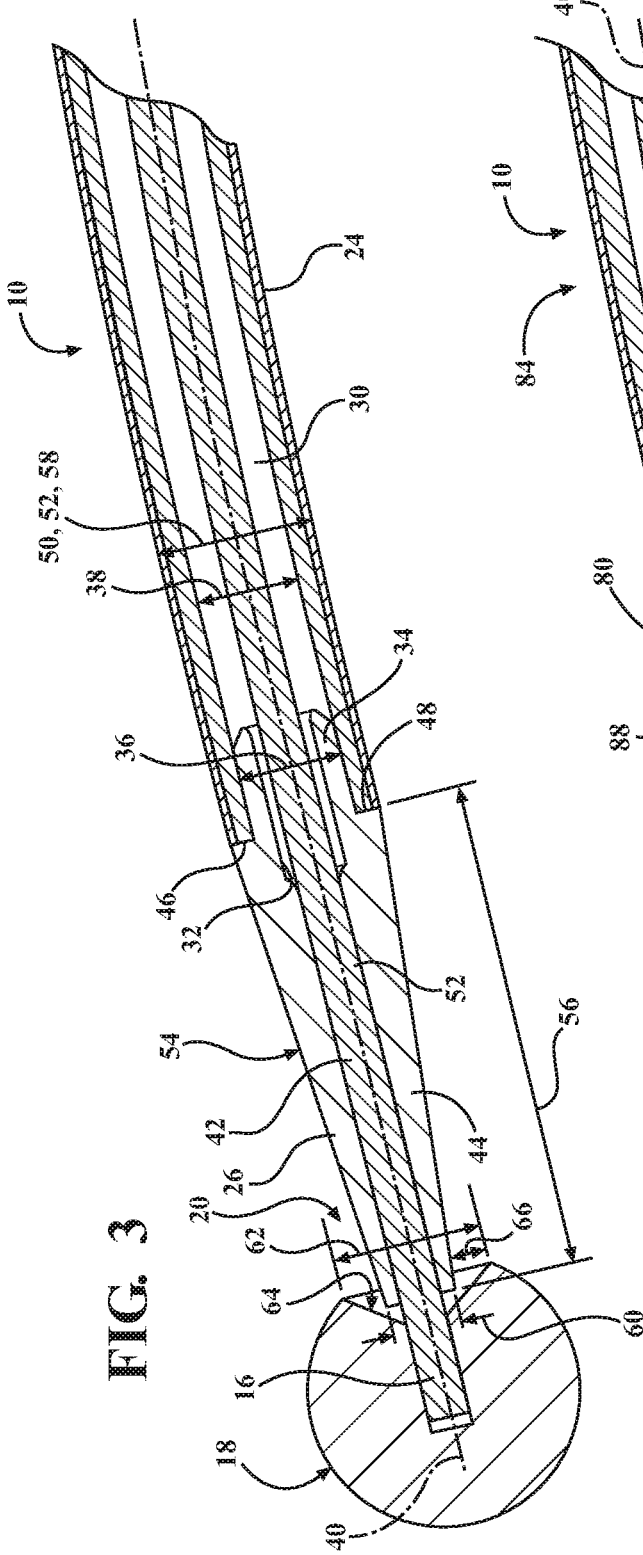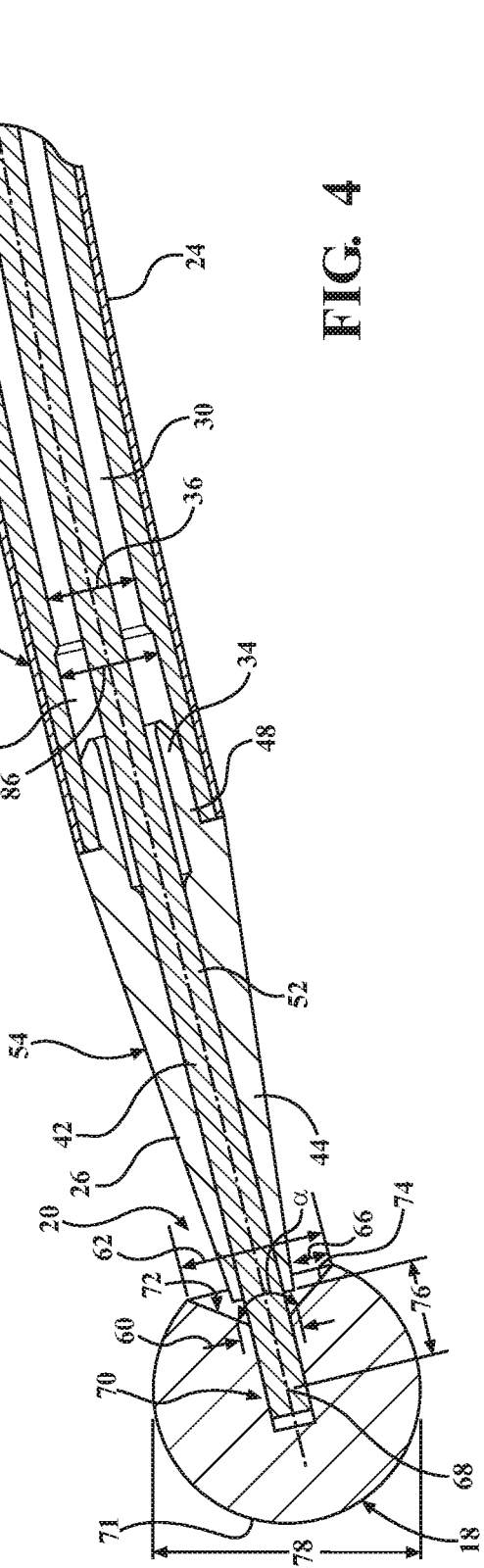

RECESSED BUR FOR A SURGICAL CUTTING TOOL

RELATED APPLICATIONS

The subject patent application is the National Stage entry of International Patent Application No. PCT/IB2019/061139, filed Dec. 19, 2019, which claims priority to and all the benefits of U.S. Provisional Patent Application No. 62/781,836, filed on Dec. 19, 2018, which is hereby incorporated by reference.

BACKGROUND

High-speed burs often include motors and attachments including a bur. The attachment with the bur must be coupled to the motor in such a way that torque can be transferred from the motor, through a driveshaft to rotate the bur at a high rate of speed to erode and/or abrade tissue of a surgical patient. While abrading the tissue of the surgical patient, loose tissue may adhere to the driveshaft of the bur, resulting in "tissue-wrapping" around the driveshaft of the bur. It is desirable to identify an apparatus that mitigates this phenomenon.

SUMMARY

The present disclosure relates to generally to surgical cutting tools for use with a handpiece having a motor. An exemplary configuration provides a surgical cutting tool including a tube that defines a lumen between proximal and distal ends. The surgical cutting tool further includes a bushing coupled to the tube at the distal end of the tube. The bushing is disposed at least partially within the lumen. The bushing defines a second lumen configured to receive a region of a driveshaft that extends past the distal end of the tube. The surgical cutting tool also includes a bur defining a recess sized to receive at least a portion of the bushing within the recess. The bur is configured to be coupled to the driveshaft.

Another exemplary configuration provides a surgical handpiece system having a handpiece assembly including a motor configured to generate torque being supported by a housing and a coupler coupled to the motor. The coupler is configured to rotate in response to the torque. The surgical handpiece system comprises a cutting tool. The cutting tool includes a tube defining a lumen. A shaft is disposed at least partially within the lumen of the tube and configured to be coupled to and driven by the coupler. The shaft has a region extending past an end of the tube. A bushing has a first portion coupled to the tube. The bushing is disposed at least partially within the lumen. The bushing defines a second lumen that receives at least a portion of the region of the shaft. The bushing has a second portion extending away from the end of the tube. A bur is coupled to the region of the shaft. The bur defines a recess sized to receive the second portion of the bushing such that the second portion of the bushing at least partially extends into the recess.

Yet another exemplary configuration provides a bur for a surgical cutting tool. The bur defines a recess. The recess has a cylindrically-shaped coupling region and a frustoconically-shaped shielding region.

BRIEF DESCRIPTION OF THE DRAWINGS

FIG. 3 is a cross-sectional view of a first instance of the end of the surgical cutting tool of FIG. 1 taken along lines 3-3 in FIG. 2.
FIG. 4 is a cross-sectional view of a second instance of the end of the surgical cutting tool of FIG. 1 taken along lines 3-3 in FIG. 2.

DETAILED DESCRIPTION

Figure 1:
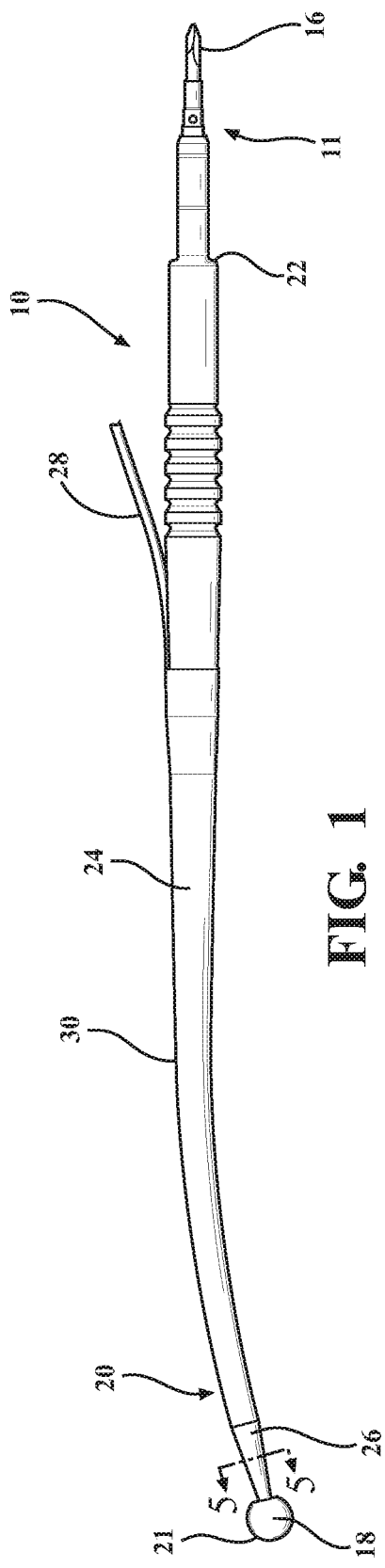
FIG. 1 is an elevation view of a surgical cutting tool.

Referring to FIG. 1, an elevation view of a surgical cutting tool 10 is shown. The surgical cutting tool 10 includes a driveshaft 16. The driveshaft 16 comprises a drive portion 11 configured to couple to a coupler such as a drive chuck (not shown) to receive torque from a motor. The driveshaft 16 is configured to transmit torque to a bur 18 coupled to a distal end of the driveshaft 16. The surgical cutting tool 10 comprises a nose tube 24 defining a lumen 30 (see FIGS. 3 and 4). The driveshaft 16 extends through the lumen 30 of the nose tube 24. The driveshaft 16 also extends through a bushing 26 coupled to the nose tube 24. Specifically, the driveshaft 16 is configured to transmit torque, from the drive chuck, and within the nose tube 24 and the bushing 26, to cause the bur 18 to rotate at a high rate of speed. In one configuration, a surgical handpiece system may include the surgical cutting tool 10. The surgical handpiece system may have a handpiece assembly that includes the motor and the coupler disposed in a housing. The motor may be configured to generate torque to rotate the coupler.

The bur 18 is shaped to abrade a surface of a material. Specifically, the bur 18 may be configured to abrade a bone material. Moreover, as will be explained in more detail below, the bur 18 may be configured to abrade a relatively small surface area of a bone, or soft tissue such as cartilage found in a nose of a patient (not shown). The bur 18 may define a spherical, ball shape having a small diameter. The bur 18 may instead define a match-head or acorn shape with abrasive or cutting geometry. The small diameter of the bur 18 allows the bur 18 to be used in applications requiring surgical precision for small and difficult areas of a human body, such as a nose, spine and skull. It is contemplated that other burs having different cutting geometry to those described above may be substituted. Again, as will be described in more detail below, the bur 18 is coupled to the distal end of the driveshaft 16. The bur 18 may be welded, adhered, or brazed to the driveshaft 16 to couple the bur 18 to the driveshaft 16 to allow torque transmission to the bur 18. Alternatively, the bur 18 may be integrally formed with the driveshaft 16. The bur 18 spins at the same rate as the driveshaft 16 when torque is applied to the driveshaft 16.

The bur 18 and the driveshaft 16 are separate from the bushing 26 and the nose tube 24. Being separate from the bushing 26 and the nose tube 24 allows the driveshaft 16 to transmit torque through the bur 18 independently of the bushing 26 and the nose tube 24. Said differently, the driveshaft 16 and the bur 18 are configured to rotate within the lumen 30 of the nose tube 24 relative to the nose tube 24 and the bushing 26.

The surgical cutting tool 10 may be equipped with an irrigation tube 28 disposed on an outer periphery of the nose tube 24. The irrigation tube 28 may be configured to cool, or irrigate an area of a patient during abrasion by the bur 18. Therefore, by allowing the bur 18 to spin independently of the bushing 26 and the nose tube 24, the irrigation tube 28 may further allow for improved surgical precision of the bur 18 by providing cooling as well as a clear surface, through channeling a fluid along the nose tube 24, for abrasion by the bur 18. In the configuration illustrated in FIGS. 1-4, the irrigation tube 28 is positioned around the nose tube 24 and extends along the nose tube 24 from a point between proximal and distal ends of the nose tube 24 to the distal end of the nose tube 24. In other configurations, the irrigation tube 28 may be positioned along an entire length of the nose tube 24, positioned between the proximal and distal ends of the nose tube 24, or positioned to extend past one or both the proximal and distal ends of the nose tube 24. It is also contemplated that an irrigation tube different from the irrigation tube 28 disclosed and illustrated may be used. Fluid travels through the irrigation tube to the distal end of the nose tube 24 to cool and clean a cutting surface 21 of the bur 18. Fluid that travels through the irrigation tube 28 to the distal end of the nose tube 24 may also aid in cleaning the bur 18 during use. It is also contemplated that in some configurations, the surgical cutting tool 10 may not include an irrigation tube 28.

Figure 2:
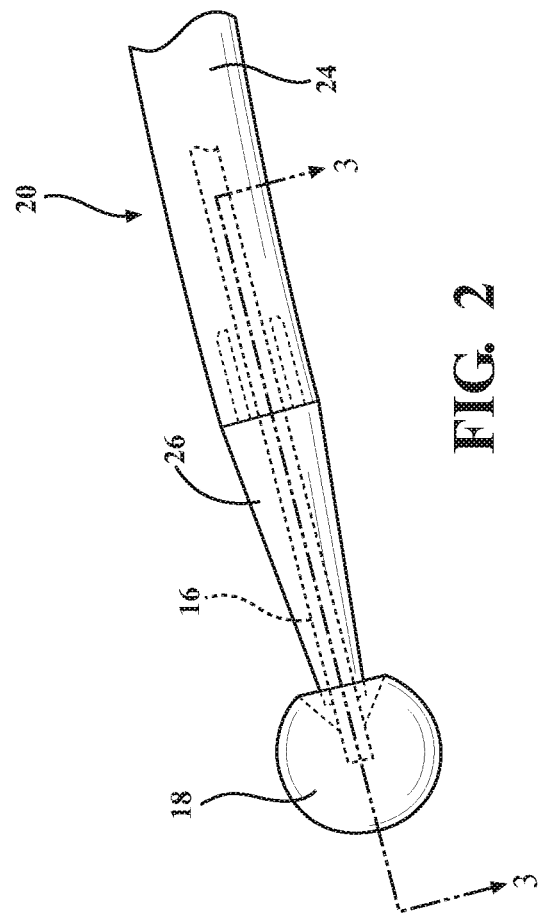
FIG. 2 is a partial, elevation view of an end of the surgical cutting tool of FIG. 1.

FIG. 2 depicts a partial, elevation view of the distal portion 20 of the surgical cutting tool 10, including a distal portion of the nose tube 24, the bushing 26, and the bur 18 being coupled to the driveshaft 16. As can be seen with reference to FIG. 2, the bushing 26 is disposed partially within the bur 18. The bur 18 may be considered a recessed bur 18, in which the bur 18 is configured to receive the bushing 26 within a recess, described in detail with reference to the other Figures, defined within the bur 18. With the bushing 26 being at least partially disposed within the bur 18, the driveshaft 16 may be protected during use. For example, the bushing 26 being disposed at least partially within the bur 18 protects the driveshaft 16 from becoming entangled in fibrous material, such as loose tissue, that is removed from the patient due to the abrasion from the bur 18.

When abrading soft tissue with the conventional burs, loose material adheres to the driveshaft. Specifically, when the driveshaft is spinning and contacts tissue, surface adhesion causes the loose tissue to bind on the driveshaft. Loose tissue binding on the driveshaft causes the loose tissue to wrap around the driveshaft. When the loose tissue wraps around the driveshaft due to the high rate of spin of the driveshaft, tension between the loose tissue and the driveshaft increases. The increase in tension between the loose tissue and the driveshaft may continue until the driveshaft experiences adverse effects. The configuration of the bur 18 receiving the bushing 26 mitigates exposure of the driveshaft 16 to tissue of the patient. Therefore, at least partially receiving the bushing 26 into the bur 18, the driveshaft 16 is not as exposed, and the loose tissue is less likely to bind to the driveshaft 16. In other words, in such a configuration, there is no portion of the driveshaft 16 that is exposed to tissue because the portion of the driveshaft 16 that is between the bur 18 and the nose tube 24 is surrounded by the bushing 26. This mitigates the occurrence of tissue-wrapping and reduces potential trauma during use.

In addition, when abrading a bone material at a high rate of rotation, the bur 18 generates heat. Heat generation may be exacerbated in instances when the surgical cutting tool 10 does not include an irrigation tube 28, as described above, when abrading a bone material. When the bur 18 abrades a bone material, the driveshaft 16 heats via conduction. The driveshaft 16 may incidentally conduct heat to other, critical structures near where the bur 18 is abrading the bone material. These critical structures, such as nerves or arteries, may be sensitive to heating via the driveshaft 16, in which the heating from the driveshaft 16 may cause adverse effects on the critical structures of a patient.

By at least partially disposing the bushing 26 in the bur 18, the driveshaft 16 is surrounded by a non-rotating structure, such as the bushing 26. The bushing 26 may comprise a low-friction material such as a ceramic, a polyetheretherketone ("PEEK"), a polytetrafluoroethylene ("PTFE"), a glass, a sapphire, a stainless steel or other materials that reduce heat from friction. Using a low friction material, the bushing 26 mitigates heat generation when the driveshaft 16 rotates against inner walls of the bushing 26. Mitigating heat generation between the driveshaft 16 and the bushing 26 reduces a possibility that the driveshaft 16 conductively transmits heat into the critical structures, such as nerves or arteries, reducing adverse effects of abrading bone material with the bur 18.

Referring to FIG. 3, the distal portion 20 of the surgical cutting tool 10 is depicted in a cross-sectional view taken along lines 3-3 in FIG. 2. Specifically, FIG. 3 depicts the driveshaft 16 extending through the lumen 30 defined of the nose tube 24, and a second lumen 32 defined by the bushing 26. The first and second lumens 30, 32 are in communication with each other to permit the driveshaft 16 to be received within. The second lumen 32 is configured to receive a region 42 of the driveshaft 16 that extends past the distal end of the nose tube 24. The first and second lumens 30, 32 allow the driveshaft 16 to rotate while the bushing 26 and nose tube 24 remain stationary.

As can be seen with reference to the cross-sectional view depicted in FIG. 3, the bushing 26 is at least partially disposed with the first lumen 30 defined in the nose tube 24. The bushing 26 may be press-fit within the first lumen 30 defined in the nose tube 24. In other instances, the bushing 26 may be welded, adhesively bonded, or otherwise fixed to the nose tube 24. In other configurations, the bushing 26 may be coupled to the nose tube 24 by a fastener or in another releasable coupling manner. More specifically, the bushing 26 is coupled to the nose tube 24 within the first lumen 30 via a first portion 34 of the bushing 26. The first portion 34 of the bushing 26 may have an outer diameter 36 being equal to or slightly greater than an inner diameter 38 of the first lumen 30. This allows the first portion 34 of the bushing 26 to be disposed within the first lumen 30 of the nose tube 24, such that the bushing 26 is press-fit into the nose tube 24. For example, the first portion 34 of the bushing 26 may press against the nose tube 24 within the first lumen 30 to maintain a position of the bushing 26. In addition, the outer diameter 36 of the first portion 34 of the bushing 26 being greater than an inner diameter 38 of the first lumen 30 of the nose tube 24 may assist in aligning the driveshaft 16, the bushing 26 and the nose tube 24 along a central axis 40 to reduce axial misalignment during rotation of the driveshaft 16. In other configurations, the first portion 34 of the bushing 26 may be positioned end to end with the nose tube 24 such that the bushing is not disposed within the first lumen 30 of the nose tube 24, but the first and second lumens 30, 32 may still be in communication with each other. In further configurations, the first portion 34 of the bushing 26 may be larger than an outer diameter of the nose tube such that the distal end of the nose tube is disposed within the second lumen 32 of the bushing 26 and the first and second lumens 30, 32 may still be in communication with each other.

The bushing 26 further includes a second portion 44 extending from the first portion 34. The second portion 44 extends such that a surface 46 of the second portion 44 of the bushing 26 abuts a distally-facing, end surface 48 of the nose tube 24. In the configuration illustrated, the surface 46 of the bushing 26 extends such that an outer surface of the bushing 26 is flush with an outer surface of the irrigation tube 28 disposed around the nose tube 24. In other configurations, the surface 46 of the bushing 26 extends such that the outer surface of the bushing 26 is flush with an outer surface of the nose tube 24. More specifically, the second portion 44 of the bushing 26 extends to an outer diameter 50 that approximates an outer diameter 52 of the nose tube 24 and/or the irrigation tube 28 defined at an outer surface of the nose tube 24 and/or the irrigation tube 28 where the surface 46 of the bushing 26 abuts the end surface 48 of the nose tube 24. Approximating the outer diameter 50 of the surface 46 of the bushing 26 with the outer diameter 52 of the nose tube 24 and/or the irrigation tube 28 allows the surgical cutting tool 10 to provide a uniform connection between the bushing 26 and the nose tube 24. Such uniformity between the bushing 26 and the nose tube 24 may further allow for increased surgical precision. For example, when the outer diameter 50 of the surface 46 of the bushing 26 approximates the outer diameter 52 of the nose tube 24 and/or the irrigation tube 28, the nose tube 24 and bushing 26 define a curvature 54, discussed in more detail below, that allows for better viewing and easier insertion of the bur 18 in a patient's nose, for example. Easier insertion of the bur 18 into a nose allows the user to abrade a soft tissue, or bone material with greater precision and improved line-of-sight.

The second portion 44 of the bushing 26 may be tapered. The second portion 44 of the bushing 26 may taper with a decreasing diameter toward the bur 18 from the nose tube 24. Therefore, the surface 46 of the bushing 26 with an outer diameter 50 that approximates an outer diameter 52 of the nose tube 24 and/or irrigation tube 28 represents a maximum diameter 58 of the bushing 26. The bushing 26 may taper incrementally such that the diameter of the bushing 26 decreases, relative to the central axis 40, in set amounts according to a set distance along a shallow curvature 54 across a length 56 of the second portion 44 of the bushing 26. Alternatively, the bushing 26 may taper acutely such that the diameter of the bushing 26 decreases, relative to the central axis 40, with a steep curvature 54 defined along the length 56 of the bushing 26. For example, the bushing 26 may define a curvature 54 that decreases to an adequate diameter within the bur 18, discussed in more detail below. As stated above, allowing easier insertion of the bur 18, due to the curvature 54, increases surgical precision and improves user line-of-sight, and the curvature 54 may be defined to enhance insertion of the bur 18 into a nose, for example.

The second portion 44 of the bushing 26 tapers such that a minimum diameter 60 of the second portion 44 of the bushing 26 is less than a width 62 of a recess 64 defined within the bur 18. Again, the second portion 44 of the bushing 26 extends into the recess 64 defined in the bur 18 to protect the driveshaft 16 from becoming entangled by loose, abraded tissue during use. For example, by providing a clearance 66 between the second portion 44 of the bushing 26 and the bur 18, the bur 18 is configured to rotate with the driveshaft 16, while the bushing 26 remains stationary.

FIG. 4 depicts a sectional view of an alternative distal portion 20 of the surgical cutting tool 10 taken along lines 3-3 of FIG. 2. FIG. 4 depicts the nose tube 24 defining a countersink feature 88 for the first portion 34 of the bushing 26. The countersink feature 88 may be a countersunk bore. In other instances, the countersink feature 88 may include other shapes that allow the first portion 34 of the bushing 26 to extend into the first lumen 30 defined by the nose tube 24. The nose tube 24 may include a distal portion 80 extending proximally from the distal end of the nose tube to define the countersink feature 88 and a proximal portion 84 disposed between the distal portion 80 and a proximal end of the nose tube 24. The distal portion 80 has an inner diameter 86 that is greater than the inner diameter 38 of the lumen 30 defined in the proximal portion 84 of the nose tube 24.

The countersink feature 88 allows the first portion 34 of the bushing 26 to extend into the first lumen 30 defined in the nose tube 24. Again, the first portion 34 of the bushing 26 may be press-fit into the lumen 30 of the nose tube 24 to secure the bushing 26 within the lumen 30 of the nose tube 24.

Referring to FIG. 4, the recess 64 defined within the bur 18 may be conically tapered toward a center 68 of the bur 18. Stated differently, the recess 64 may define an angle a between internal surfaces 74 of the recess 64 defined in the bur 18, wherein the internal surfaces 74 slant away from each other toward an outer periphery 71 of the bur 18. The angle a of the recess 64 defined within the bur 18 may also define the width 62 of the recess 64. The width 62 of the recess 64 defined within the bur 18 is greater than the minimum diameter 60 of the second portion 44 of the bushing 26.

Again, the width 62 of the recess 64 is greater than a minimum diameter 60 of the second portion 44 of the bushing 26 to allow the bur 18 and driveshaft 16 to rotate independently of the bushing 26. Stated differently, the width 62 of the recess 64 is defined such that the bur 18 may not contact the second portion 44 of the bushing 26 during typical operation. Therefore, the width 62 of the recess 64 provides the clearance 66 from the second portion 44 of the bushing 26. The clearance 66 accounts for any radial movement of the driveshaft 16 within the recess 64 defined within the bur 18. For example, during use, the bur 18 may be exposed to bending loads at a point of contact between the bur 18 and tissue, and the clearance 66 may be defined such that the second portion 44 of the bushing 26 does not contact the bur 18 as a result of the driveshaft 16 deflecting from the bending loads. The clearance 66 between the bushing 26 and the bur 18 prevents the bushing 26 from contacting the bur 18 and therefore, prevents friction through contact between the bur 18 and bushing 26.

As stated above, the bur 18 may be coupled to the driveshaft 16 via welding, brazing or adhering. The bur 18 may be coupled to the driveshaft 16 within the recess 64. More specifically, the bur 18 may be coupled to the driveshaft 16 adjacent the center 68 of the bur 18 within a volume of the recess 64. Where the driveshaft 16 couples to the bur 18 within the volume of the recess 64 may be referred to as a coupling region 70. Therefore, the bur 18 may be coupled to the driveshaft 16 at the coupling region 70. In addition to the coupling region 70, the recess 64 defined in the bur 18 also includes a shielding region 72 that extends from the coupling region 70. The volume of the coupling region 70 may be shaped differently than a volume of the shielding region 72. For example, the coupling region 70 may define a volume, wherein the driveshaft 16 extends into the coupling region 70 to secure the driveshaft 16 to the bur 18, whereas the shielding region 72 may define a volume that prevents the second portion 44 of the bushing 26 from contacting the bur 18. The shielding region 72 of the recess 64 defined in the bur 18 protects the driveshaft 16, as described above. The second portion 44 of the bushing 26 is at least partially disposed in the shielding region 72.

In some configurations, the shielding region 72 has a frustoconical shape, whereas the coupling region 70 has a cylindrical shape. For example, the width 62 of the recess 64 may be such that the internal surface 74 of the recess 64 tapers with a decreasing diameter toward the center 68 of the bur 18 from the outer periphery 71 of the bur 18. Again, the width 62 and clearance 66 of the recess 64 provides shielding, through the shielding region 72, to aid in protecting the driveshaft 16 from entanglement with fibrous material such as loose tissue. While described as conical and frustoconical, the coupling and shielding regions 70, 72 may each independently define other shapes, such as spherical, cubical, cylindrical or other shapes that provide a suitable geometry to allow coupling of the driveshaft 16 to the bur 18 and further aids to prevent contact between the second portion 44 of the bushing 26 and the internal surfaces 74 of the bur 18.

Referring to FIG. 4, the shielding region 72 may be further defined based on a ratio of a distance 76 between the second portion 44 of the bushing 26 and the center 68 of the bur 18, and a diameter 78 of the bur 18. The ratio between the distance 76 and the diameter 78 of the bur 18 may be less than 5:1. Increasing beyond this 5:1 limit may increase a possibility of contact, due to bending loads exerted during use, between the second portion 44 of the bushing 26 and the internal surface 74 of the recess 64 defined in the bur 18. However, the ratio between the distance 76 and the diameter 78 of the bur 18 may include other ratios, such as 1:1, 2:1, 3:1, 4:1, or 6:1 or other ratios therebetween. The recess 64 may be defined such that the width 62 of the recess 64 accounts, through the clearance 66 described above, for radial play between the second portion 44 of the bushing 26 and the internal surface 74 of the recess 64 defined in the bur 18.

Figure 5:
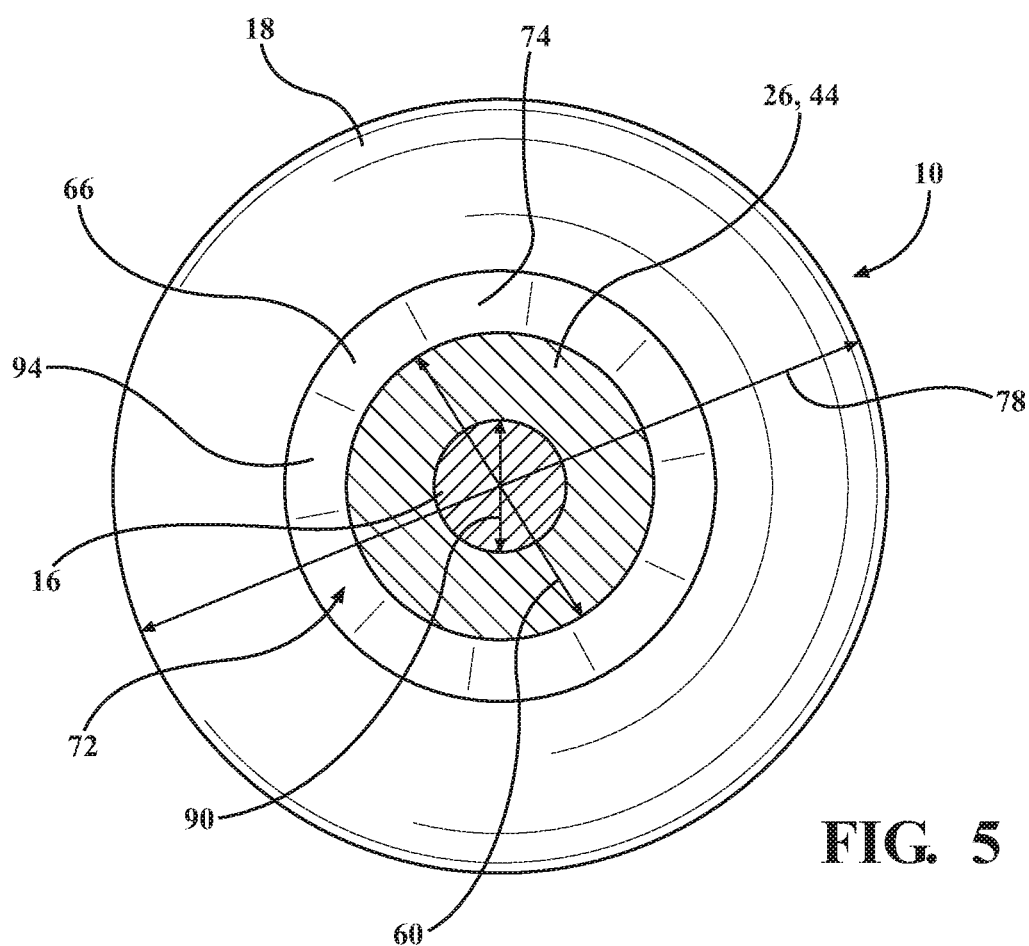
FIG. 5 is a sectional view of a bur of the surgical cutting tool of FIG. 1 taken along lines 5-5 of FIG. 1.

Referring to FIG. 5, a rear sectional view of the bushing 26, bur 18, and driveshaft 16 taken along lines 5-5 of FIG. 1 is depicted. Specifically, FIG. 5 depicts the bushing 26 partially encapsulating the driveshaft 16 with the clearance 66 between the bur 18 and the second portion 44 of the bushing 26. As can be seen with reference to FIG. 5, the driveshaft 16 has a diameter 90 being less than the minimum diameter 60 of the second portion 44 of the bushing 26. The minimum diameter 60 of the second portion 44 of the bushing 26 is also less than the width 62 of the recess 64 clearance 66 formed between the second portion 44 of the bushing 26 and the internal surface 74 of the bur 18. Again, when the clearance 66 is greater than the minimum diameter 60 of the second portion 44 of the bushing 26, the shielding region 72 of the bur 18 protects the driveshaft 16 from entangling loose tissue on the driveshaft 16.

The clearance 66 also protects the critical structures of a patient from absorbing heat from the rotating driveshaft 16. During use, heat may be conducted through the driveshaft 16 to the second portion 44 of the bushing 26. The clearance 66 may also provide cooling through a gap 94 of the shielding region 72 between the second portion 44 of the bushing 26 and the internal surface 74 of the bur 18. For example, air, or an irrigation fluid from the irrigation tube 28 may aid to cool the driveshaft 16 during use. Further, the gap 94 may aid to shield heat conduction through the second portion 44 of the bushing 26 due to rotation of the driveshaft 16 because the gap 94 of the shielding region 72 is disposed within the recess 64 defined in the bur 18.

As stated above, the ratio between the distance 76 between the second portion 44 of the bushing 26 and the center 68 of the bur 18, and the diameter 78 of the bur 18 may be less than 5:1. The diameter 78 of the bur 18 may be adjusted within the ratio, while accounting for the bending loads exhibited on the bur 18 during use. Therefore, the diameter 78 of the bur 18 may be constrained based on the distance 76 between the second portion 44 of the bushing 26 and the center 68 of the bur 18, as well based on known loads acting on the bur 18 during use of the surgical cutting tool 10. By maintaining the 5:1 ratio, the bur 18 provides the shielding region 72 within the recess 64. The shielding region 72 protects the driveshaft 16 from entanglement with loose material, prevents contact between the internal surface 74 and the second portion 44 of the bushing 26, and aids to reduce friction heat transfer to critical structures of a patient from heat conduction through the driveshaft 16 and the bushing 26.

It will be further appreciated that the terms "include," "includes," and "including" have the same meaning as the terms "comprise," "comprises," and "comprising."

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject matter of a claim dependent from one independent claim can also be implemented in connection with another independent claim.

The present disclosure also comprises the following clauses, with specific features laid out in dependent clauses, that may specifically be implemented as described in greater detail with reference to the configurations and drawings above.

I. A surgical cutting tool for use with a handpiece having a motor, comprising:
  a tube defining a first lumen between proximal and distal ends;
  a bushing coupled to the tube at the distal end, the bushing defining a second lumen in communication with the first lumen configured to receive a region of a driveshaft that extends past the distal end of the tube; and
  a bur defining a recess sized to receive at least a portion of the bushing within the recess, the bur configured to be coupled to the driveshaft.

II. The surgical cutting tool of clause I, wherein a surface of the bushing tapers with a decreasing diameter within the recess.

III. The surgical cutting tool of any of clauses I-II, wherein the bushing is coupled to the tube within the lumen via a first portion of the bushing, the first portion of the bushing having an outer diameter being greater than an inner diameter of the lumen.

IV. The surgical cutting tool of clause III, wherein the tube has a distal portion adjacent the distal end and a proximal portion disposed between the distal portion and the proximal end, the distal portion having a second inner diameter being greater than the inner diameter of the proximal portion.

V. The surgical cutting tool of any of clauses III-IV, wherein the bushing has a second portion adjacent to the first portion such that a surface of the bushing abuts a distally-facing end surface of the tube.

VI. The surgical cutting tool of clause V, wherein the second portion of the bushing extends to an outer diameter that approximates an outer diameter of the tube defined at an outer surface of the tube.

VII. The surgical cutting tool of any of clauses I-VI, wherein the recess defined in the bur has an internal surface having a cylindrical coupling region to couple the bur to the driveshaft and a frustoconical shielding region that receives the portion of the bushing.

VIII. The surgical cutting tool of clause VII, wherein the frustoconical shielding region of the internal surface tapers with a decreasing diameter toward the coupling region.

What is claimed is:

1. A surgical cutting tool for use with a handpiece having a motor, comprising:
   a tube defining a lumen between proximal and distal ends;
   a driveshaft;
   a bushing coupled to the tube at the distal end and disposed at least partially within the lumen, the bushing defining a second lumen configured to receive a region of the driveshaft that extends past the distal end of the tube; and
   a bur defining a recess sized to receive at least a portion of the bushing within the recess, the bur coupled to the driveshaft.

2. The surgical cutting tool of claim 1, wherein a surface of the bushing tapers with a decreasing diameter within the recess.

3. The surgical cutting tool of claim 1, wherein the bushing is coupled to the tube within the lumen via a first portion of the bushing, the first portion of the bushing having an outer diameter being greater than an inner diameter of the lumen.

4. The surgical cutting tool of claim 3, wherein the tube has a distal portion adjacent the distal end and a proximal portion disposed between the distal portion and the proximal end, the distal portion having a second inner diameter being greater than the inner diameter of the proximal portion.

5. The surgical cutting tool of claim 3, wherein the bushing has a second portion adjacent to the first portion such that a surface of the bushing abuts a distally-facing end surface of the tube.

6. The surgical cutting tool of claim 5, wherein the second portion of the bushing extends to an outer diameter that approximates an outer diameter of the tube defined at an outer surface of the tube.

7. The surgical cutting tool of claim 1, wherein the recess defined in the bur has an internal surface having a cylindrical coupling region to couple the bur to the driveshaft and a frustoconical shielding region that receives the portion of the bushing.

8. The surgical cutting tool of claim 7, wherein the frustoconical shielding region of the internal surface tapers with a decreasing diameter toward the coupling region.

9. A surgical handpiece system having a handpiece assembly including a motor configured to generate torque being supported by a housing and a coupler coupled to the motor, and configured to rotate in response to the torque comprising:
   a cutting tool including:
   a tube defining a lumen;
   a shaft being disposed at least partially within the lumen of the tube and configured to be coupled to and driven by the coupler, the shaft having a region extending past an end of the tube;
   a bushing having a first portion coupled with the tube being disposed at least partially within the lumen, the bushing defining a second lumen that receives at least a portion of the region of the shaft, and a second portion extending away from the end of the tube; and
   a bur coupled to the region of the shaft, and defining a recess sized to receive the second portion of the bushing such that the second portion of the bushing at least partially extends into the recess.

10. The surgical handpiece system of claim 9, wherein the second portion of the bushing tapers with a decreasing diameter toward the bur.

11. The surgical handpiece system of claim 9, wherein the bushing is coupled to the tube within the lumen via the first portion of the bushing having an outer diameter being greater than an inner diameter of the lumen.

12. The surgical handpiece system of claim 9, wherein the recess defined in the bur has an internal surface having a coupling region configured to be coupled to the shaft and a shielding region that receives the portion of the bushing, the coupling region and the shielding region being shaped differently from one another.

13. The surgical handpiece system of claim 12, wherein the shielding region of the internal surface tapers with a decreasing diameter toward the coupling region.

14. The surgical handpiece system of claim 12, wherein the recess defined within the bur is conically sized with an angle defining a width of the recess being greater than an outer diameter of at least the second portion of the bushing within the shielding region.

15. The surgical handpiece system of claim 12, wherein the coupling region is defined at a distance from the second portion of the bushing disposed within the recess.

\* \* \* \* \*